(12) United States Patent
Stypulkowski

(10) Patent No.: US 7,873,418 B2
(45) Date of Patent: *Jan. 18, 2011

(54) VARIATION OF NEURAL STIMULATION PARAMETERS

(75) Inventor: Paul H. Stypulkowski, North Oaks, MN (US)

(73) Assignee: Medtronic, Inc., Minneapolis, MN (US)

( * ) Notice: Subject to any disclaimer, the term of this patent is extended or adjusted under 35 U.S.C. 154(b) by 1137 days.

This patent is subject to a terminal disclaimer.

(21) Appl. No.: 11/380,857

(22) Filed: Apr. 28, 2006

(65) Prior Publication Data

US 2006/0190061 A1  Aug. 24, 2006

Related U.S. Application Data

(63) Continuation of application No. 10/044,405, filed on Jan. 11, 2002, now Pat. No. 7,050,856.

(51) Int. Cl.
*A61N 1/36* (2006.01)

(52) U.S. Cl. ....................................................... 607/45

(58) Field of Classification Search ............. 607/44–47, 607/63, 64, 66–76
See application file for complete search history.

(56) References Cited

U.S. PATENT DOCUMENTS

| | | |
|---|---|---|
| 2,350,797 A | 6/1944 | Morland |
| 3,489,152 A | 1/1970 | Barbara |
| 3,650,277 A | 3/1972 | Sjostrand |
| 3,822,708 A | 7/1974 | Zilber |
| 3,954,111 A | 5/1976 | Sato |
| 3,983,881 A | 10/1976 | Wickham |
| 4,121,594 A | 10/1978 | Miller |
| 4,153,059 A | 5/1979 | Fravel |
| 4,210,151 A | 7/1980 | Keller, Jr. |
| 4,338,945 A | 7/1982 | Kosugi |
| 4,390,023 A | 6/1983 | Rise |
| 4,431,000 A | 2/1984 | Butler |
| 4,541,432 A | 9/1985 | Molina-Negro |
| 4,556,064 A | 12/1985 | Pomeranz |

(Continued)

FOREIGN PATENT DOCUMENTS

EP  0160753  11/1985

(Continued)

OTHER PUBLICATIONS

O.M. Rutherford and D.A. Jones, Contractile Properties and Fatigu-ability of the Human Adductor Pollicis and First Dorsal Interosseus: A Comparison of the Effects of Two Chronic Stimulation Patterns, Journal of the Neurological Sciences, 85, 319-331 (1988).

*Primary Examiner*—George R Evanisko
(74) *Attorney, Agent, or Firm*—Banner & Witcoff, Ltd.

(57) ABSTRACT

Techniques for varying stimulus parameters used in neural stimulation to improve therapy efficacy, minimize energy consumption, minimize undesired side effects, and minimize loss of therapeutic effectiveness due to physiologic tolerance to stimulation. Neural stimulation is provided having a stimulation amplitude, a stimulation frequency, a stimulation pulse duration, an electrode-firing pattern, and a set of electrode-firing-polarity conditions. At least one of the stimulation parameters is pseudo-randomly varied. A second stimulation parameter is changed based upon having pseudo-randomly varied the first stimulation parameter and based upon a predetermined relationship specifying how changes in the first parameter affect desirable values for the second parameter.

11 Claims, 6 Drawing Sheets

U.S. PATENT DOCUMENTS

| | | |
|---|---|---|
| 4,686,991 A | 8/1987 | Dufresne |
| 4,699,143 A | 10/1987 | Dufresne |
| 4,706,674 A | 11/1987 | Dieken |
| 4,887,603 A | 12/1989 | Morawetz |
| 4,922,908 A | 5/1990 | Morawetz |
| 5,069,211 A | 12/1991 | Bartelt |
| 5,269,304 A | 12/1993 | Matthews |
| 5,683,422 A | 11/1997 | Rise |
| 5,755,749 A | 5/1998 | Sakano |
| 5,792,212 A | 8/1998 | Weijand |
| 6,188,929 B1 | 2/2001 | Giordano |
| 6,466,822 B1 | 10/2002 | Pless |
| 6,690,974 B2 | 2/2004 | Archer |
| 6,701,190 B2 | 3/2004 | Gliner |
| 7,050,856 B2 * | 5/2006 | Stypulkowski ............... 607/45 |
| 2002/0055762 A1 * | 5/2002 | Gliner ........................ 607/46 |
| 2003/0093134 A1 | 5/2003 | Bradley |
| 2004/0102820 A1 * | 5/2004 | Moune et al. ................. 607/48 |

FOREIGN PATENT DOCUMENTS

| | | |
|---|---|---|
| FR | 2500309 | 8/1982 |
| GB | 2163355 | 2/1986 |
| GB | 2255719 | 11/1992 |
| WO | 0230509 | 4/2002 |

* cited by examiner

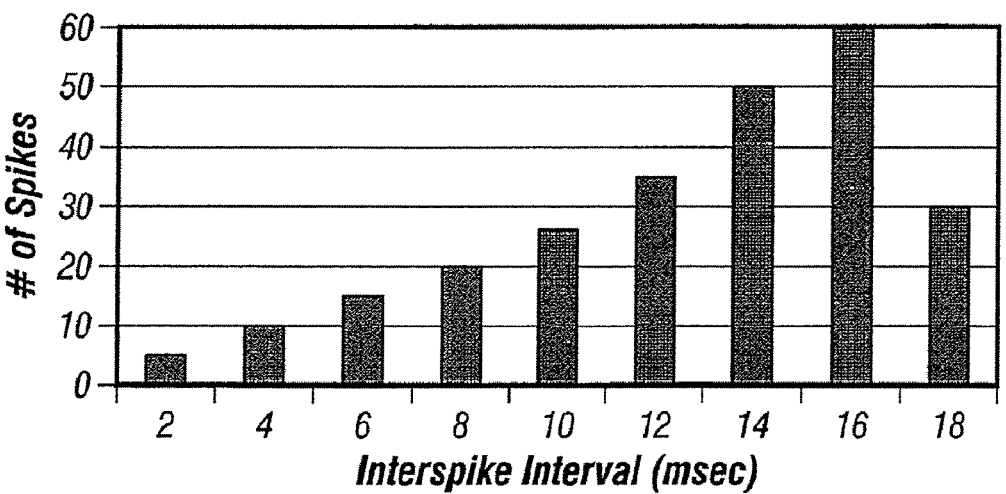
FIG. 8
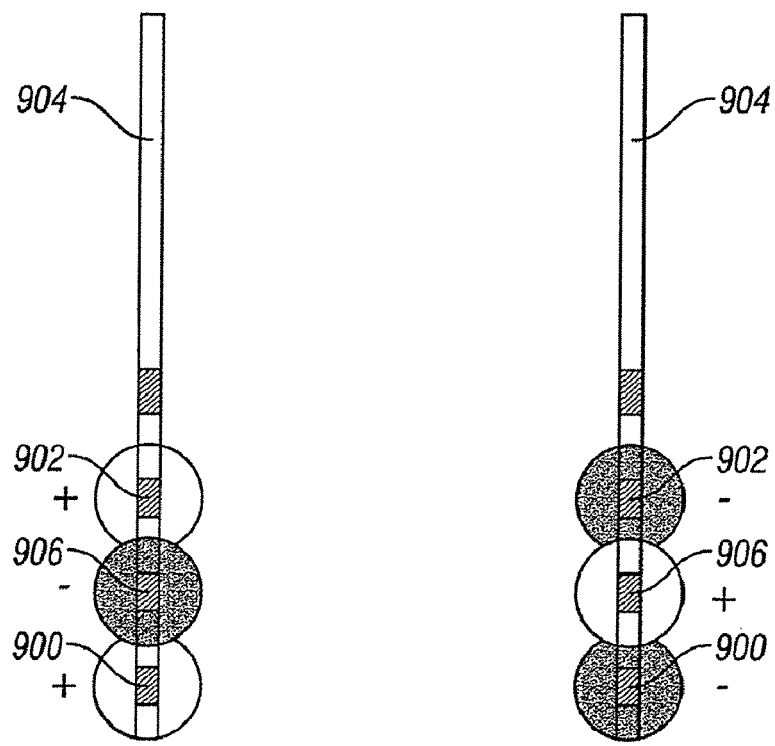
FIG. 9A  FIG. 9B

VARIATION OF NEURAL STIMULATION PARAMETERS

This application is a continuation of application Ser. No. 10/044,405 filed on Jan. 11, 2002. The entire disclosure of which is hereby incorporated by reference.

FIELD OF THE INVENTION

The invention relates to dynamically changing various neural-stimulation-treatment parameters to improve therapy efficacy, minimize energy consumption, minimize undesired side effects, and to minimize any loss of therapeutic efficacy due to a patient developing physiologic tolerance to therapeutic stimulation. More particularly, the invention relates to pseudo-randomly changing stimulation-parameter values such as frequency, amplitude, pulse width, electrode-firing pattern, and electrode-firing-polarity conditions while therapeutically treating a patient with neural stimulation.

BACKGROUND OF THE INVENTION

Neural stimulation devices are capable of treating various disorders and symptoms of disorders. In the context of neural stimulators, an electrical lead having one or more electrodes is typically implanted near a specific site in the brain of a patient. The lead is coupled to a signal generator that delivers electrical energy through the electrodes to nearby neurons and neural tissue. The electrical energy delivered through the electrodes creates an electrical field causing excitation or inhibition of the nearby neurons to directly or indirectly treat the neurological disorder or symptoms of the disorder.

Experience with deep-brain stimulation (DBS) in the treatment of movement disorders and epilepsy has indicated that, in some cases, patients develop a tolerance or adaptation to the stimulation. A possible cause underlying this long-term habituation may be related to the fact that the nervous system tends to adapt to constant, non-varying inputs and eventually ignores them. In much the same way that tolerance to drugs can develop, tolerance to stimulation may occur with repeated, long-term use.

Conventional stimulus patterns for DBS and other neural-stimulation applications often employ a fixed-frequency, fixed-amplitude, fixed-pulse-width, and fixed-electrode-firing-pattern combination for a given patient. This can result in the same population of neurons being repeatedly activated or inhibited with very little temporal or spatial variation. Such a pattern of activity is highly artificial and non-physiologic compared to the recorded firing patterns of normal neurons.

An example of a method and apparatus employing varying stimulation patterns to reduce the effects of neurodegenerative disorders can be found in U.S. Pat. No. 5,683,422, which is incorporated herein by reference. The '422 patent discloses a closed loop feedback control algorithm for both blocking and facilitating neural activity at a stimulation site. A clinician programs a range of values for pulse width, amplitude, and frequency that the stimulation device uses to optimize the therapy. For blocking neuronal activity, if the feedback sensor values indicate too much activity, the stimulation frequency is increased up to a preset maximum value. If the frequency parameter is at the maximum value, the algorithm next increases the pulse width up to a preset maximum value. Once the maximum pulse width has been reached, the algorithm next increases amplitude in a like manner. Once all parameters reach the maximum value, a notification message is sent to the clinician.

If activation of the stimulation site is desired, the frequency parameter is fixed at a value chosen by the clinician to facilitate neuronal activity. The values from the feedback sensor are used to determine whether neuronal activity is being adequately controlled. Inadequate control indicates that the neuronal activity of the stimulation target is too low. Neuronal activity is increased by first increasing stimulation amplitude up to a predetermined maximum value. When the maximum amplitude is reached, the algorithm increases pulse width to its maximum value. If the maximum parameters provide insufficient stimulation, the clinician is notified.

An additional algorithm readjusts parameter levels downward as far as possible. When parameters are changed, a timer is reset. If there is no need to change any stimulus parameters before the timer has counted out, then parameter values are reduced while still maintaining appropriate levels of the neuronal activity. The various parameter values are reduced until the sensor values indicate a need to increase them.

The '422 patent, however, does not address the problem of development of a physiological tolerance to the stimulation. In the '422 patent, if the neural activity remains constant and the stimulation parameters have been adjusted down to their lowest possible values, no further adjustments are made to any of the stimulation parameters. The stimulation patterns can therefore become regular or constant and a patient can develop a physiological tolerance to the treatment. The stimulation produced by the system of the '422 patent also results in a regular firing pattern (i.e., at a fixed frequency) which tends to differ from the recorded firing patterns of normal neurons, as described above. A need therefore exists for techniques of using stimulation patterns that are less regular and more random in nature, similar to the firing patterns seen in a normal nervous system.

Certain types of therapeutic stimulation may require that a relatively large volume of neural tissue be modulated by the stimulation. This may require a high level of battery power, which in turn may require that implanted neurostimulation treatment devices be explanted to replace a depleted battery. For instance, obsessive-compulsive disorder is often treated with four electrodes placed in a specific brain structure, with each electrode stimulated at a relatively high current, which causes a large drain on an implanted stimulator's battery. There is a need, therefore, for treatment techniques that reduce the amount of battery current required by minimizing the amount of energy utilized, while maintaining the desired therapy efficacy. Similarly, it may not be possible to achieve the desired therapeutic effect without undesired side effects of stimulation when a large volume of tissue is simultaneously modulated. By pseudo-randomly varying the spatial pattern of the modulated neural structures, it may be possible to minimize undesired side-effects while attaining the desired therapy efficacy.

BRIEF SUMMARY OF THE INVENTION

An illustrative embodiment of the invention, overcomes the above-noted, and other, shortcomings of conventional neural stimulation devices. An illustrative embodiment of the invention provides techniques for varying stimulus parameters used in deep-brain stimulation (DBS) and other types of neural stimulation to minimize loss of therapeutic effectiveness due to physiologic tolerance to stimulation.

An illustrative embodiment of the invention includes a method of reducing the loss of therapeutic efficacy in neural stimulation due to development of physiologic tolerance to the stimulation. This method includes the steps of: providing neural stimulation that has multiple stimulation parameters including a stimulation amplitude, a stimulation frequency, a stimulation pulse duration, and a set of one or more electrode-polarity-firing conditions; pseudo-randomly varying at least a first of the stimulation parameters; and changing a value of a second stimulation parameter based upon having pseudo-randomly varied the first stimulation parameter and based upon a predetermined relationship that specifies how changes in the first parameter affect desirable values for the second parameter.

As used herein, the terms "pseudo-random" or "pseudo-randomly" mean any quasi random or effectively random output generated by a system, such as software running on a microprocessor (e.g., random number generators), and may be limited to a predetermined range of values.

The predetermined relationship may be substantially similar to a strength-duration curve for neural excitation, which may be measured for at least one of a patient's neurons by measuring multiple stimulation-amplitude values at multiple stimulation-pulse durations and observing whether a desired clinical outcome is achieved.

The first stimulation parameter may be varied to produce a neuron-firing pattern having different interspike intervals measured over different interspike-measurement durations. This can be done by varying the first stimulation parameter to produce multiple neuron-firing patterns selected from: a substantially-normal-distribution neural-firing pattern, a skew-left-distribution neural-firing pattern, a skew-right-distribution neural-firing pattern, and a bimodal-bursting-distribution neural-firing pattern.

A firing pattern of a plurality of electrodes may be pseudo-randomly varied by pseudo-randomly varying multiple electrode-firing polarity conditions among the following conditions: anode, cathode, and off.

Other advantages, novel features, and further scope of applicability of the invention will be set forth in the following detailed description.

BRIEF DESCRIPTION OF THE DRAWINGS

The accompanying drawings illustrate embodiments of the present invention and, together with the detailed description, serve to explain the principles of the invention. In the drawings, in which like numbers refer to like parts throughout:

FIG. 8 is a histogram illustrating a skew-right-distribution interspike interval.

FIGS. 9A and 9B illustrate various electrode-polarity-firing conditions in accordance with an illustrative embodiment of the invention.

DETAILED DESCRIPTION OF THE INVENTION

Figure 1:
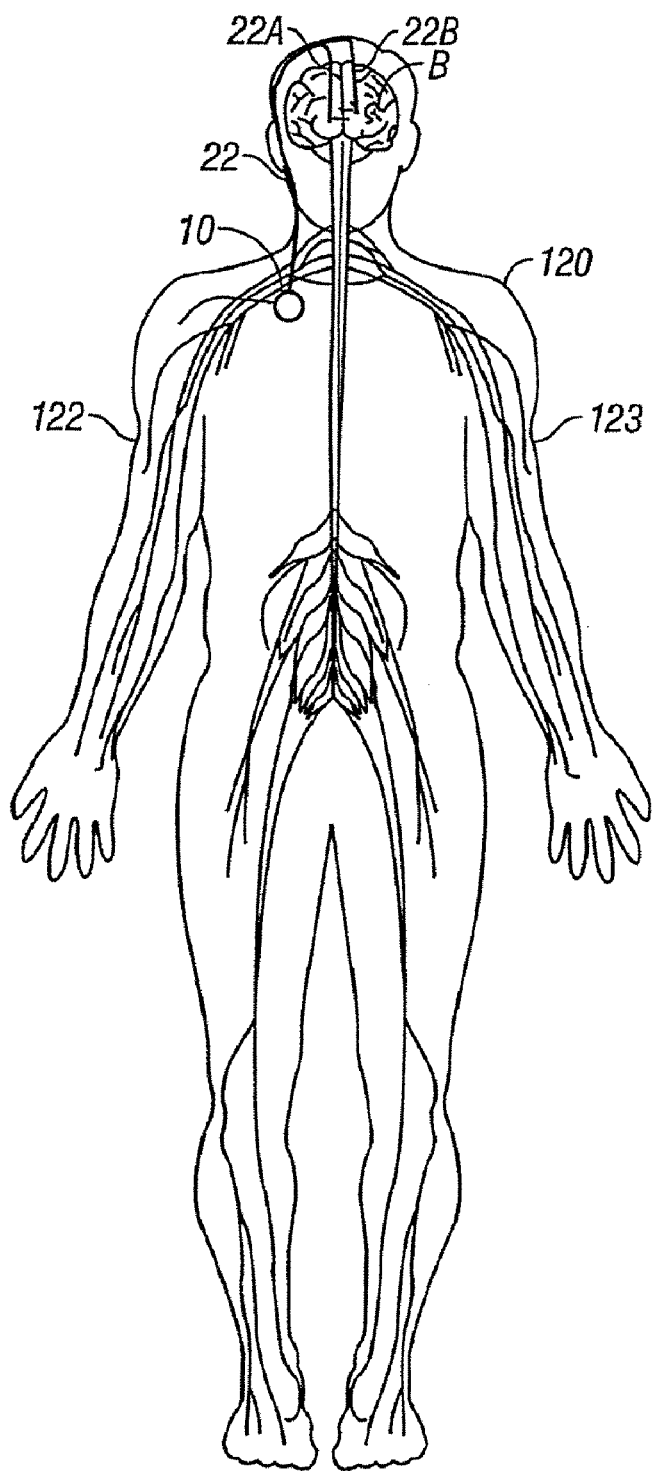
FIG. 1 depicts a neural stimulation device implanted in a person's brain in accordance with an illustrative embodiment of the invention.

FIG. 1 depicts a microprocessor-controlled neural stimulation device 10 in accordance with an illustrative embodiment of the invention. Device 10 is preferably implanted below the skin of a patient, or alternatively, may be an external device. A lead 22A is positioned to stimulate a specific site in the brain (B). Device 10 may take the form of a modified signal generator Model 7424 manufactured by Medtronic, Inc. under the trademark Itrel II. Lead 22A may be any lead suitable for stimulation. The distal end of lead 22A terminates in one or more stimulation electrodes generally implanted into a portion of the brain such as the thalamus, the internal capsule, the globus pallidus, the subthalamic nucleus or other neural structure by conventional stereotactic surgical techniques. Any number of electrodes may be used for various applications. Each of the electrodes is individually connected to device 10 through lead 22A and conductor 22. Lead 22A is surgically implanted through a hole in the skull and conductor 22 is implanted between the skull and the scalp.

Conductor 22 may be divided into twin leads 22A and 22B that are implanted into the brain bilaterally as shown in FIG. 1. Alternatively, lead 22B may be supplied with stimulation pulses from a separate conductor and signal generator.

Figure 2:
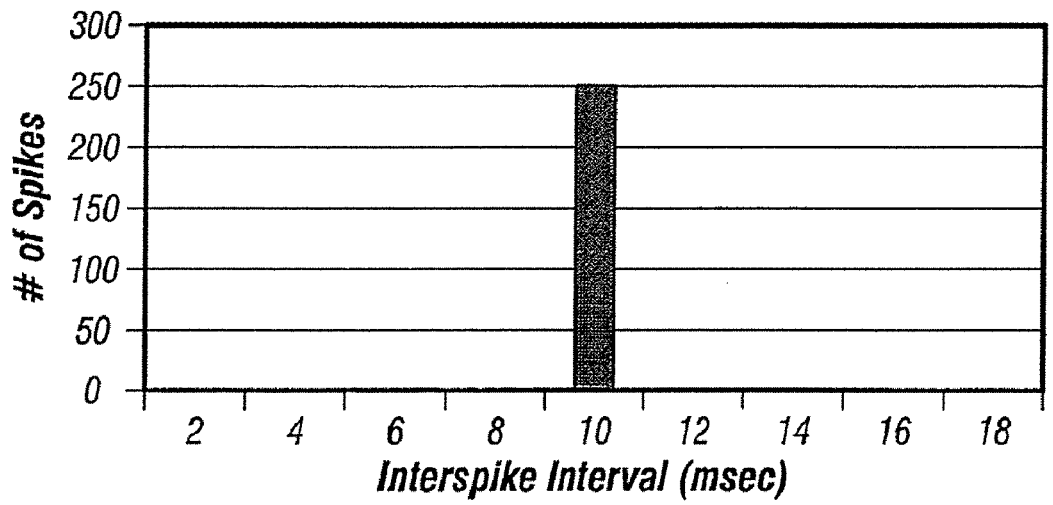
FIG. 2 is a histogram illustrating an interspike interval of a typical neuron when driven by neural stimulation.
Figure 3:
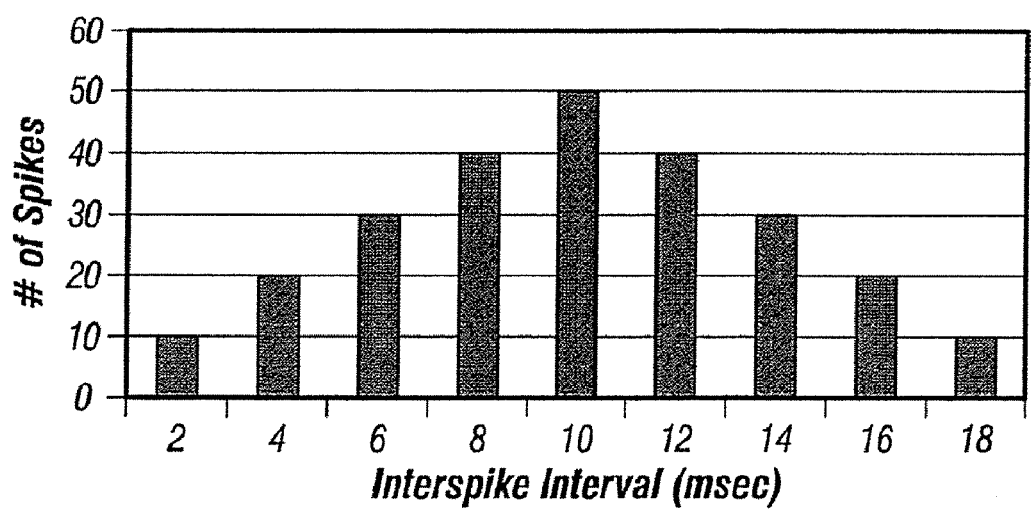
FIG. 3 is a histogram illustrating an interspike interval of a typical neuron firing normally.

FIG. 3 is a histogram of a normal-distribution interspike interval (ISI) for a typical neuron. FIG. 2 is a histogram of an ISI for a typical neuron driven with DBS. The ISI equals 1/f, where f is the instantaneous firing frequency of the neuron, and thus represents the time in milliseconds, between neural discharges, which are commonly known as action potentials or spikes. By measuring the spikes over a fixed period of time or over a fixed number of spikes, the average firing frequency of a neuron can be calculated, and the ISI data can be displayed as a histogram. In the examples of FIGS. 2 and 3, the average firing rate over a sample of 250 spikes is the same in both cases (100 Hz), but the distributions of the ISI's are very different. FIG. 3 reflects a more normal, irregular pattern, versus the highly regular discharge pattern, which is produced by DBS and which is shown in FIG. 2. Referring to FIG. 2, the output of conventional neural stimulators is often a non-varying, fixed frequency pulse train (in this example the stimulus rate is 100 Hz), which results in a fixed, non-varying ISI for the neurons being affected by the DBS. Many thousands of cells may be stimulated in DBS applications. Driving such a large population of neurons at a fixed ISI may undesirably create a very regular and highly artificial, non-physiological firing pattern. This unusually regular and artificial firing pattern may lead the patient to develop a tolerance or adaptation to the stimulation.

Figure 4:
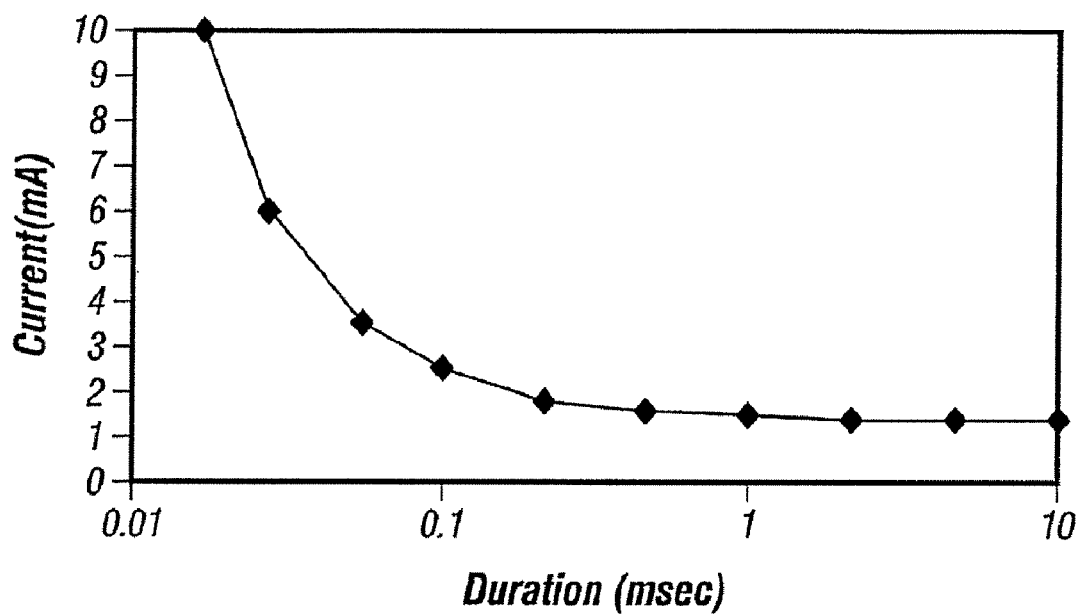
FIG. 4 is a graph of an example strength-duration curve for neural excitation.

Varying, in a random or pseudo-random fashion, one or several of the stimulus parameters advantageously creates a more natural firing pattern. A microprocessor-controlled stimulator can produce random, more natural, stimulation patterns by varying, in a predetermined relationship, the different stimulus parameters. A treating physician or other clinician may specify acceptable ranges for the various stimulus parameters such as frequency, amplitude, and pulse width. For example, it is well known that the threshold for excitation of a neuron (or a population of neurons) by an electrical stimulus depends upon both the amplitude and the pulse width of the stimulus waveform. This relationship (known as the strength-duration curve for neural excitation) can be measured for individual neurons or populations of neurons. An example strength-duration curve is shown in FIG. 4. This curve is a function of the stimulation current level and pulse duration required for excitation of one or more neurons. Such a strength-duration relationship can be determined clinically, by measuring the required stimulus current at various pulse durations to achieve some clinical outcome measure (e.g., reduction of tremor with thalamic stimulation). Once this relationship has been measured for a given electrode (or combination of electrodes) in a given patient, these data can be used to generate random or pseudo-random combinations of amplitude and pulse width values that have been determined to provide the desired clinical outcome.

As used herein, the terms "pseudo-random" or "pseudo-randomly" mean any quasi random or effectively random output generated by a system, such as software running on a microprocessor (e.g., random number generators), and may be limited to a predetermined range of values. Suitable algorithms for generating pseudo-random numbers are well known in the art. Pseudo-random numbers generated in such a manner could be used to pseudo-randomly vary one or more neural-stimulation parameters. For instance, the amplitude of the stimulation could be pseudo-randomly varied by periodically multiplying the amplitude of the neural stimulation by a different pseudo-randomly generated number.

Figure 5:
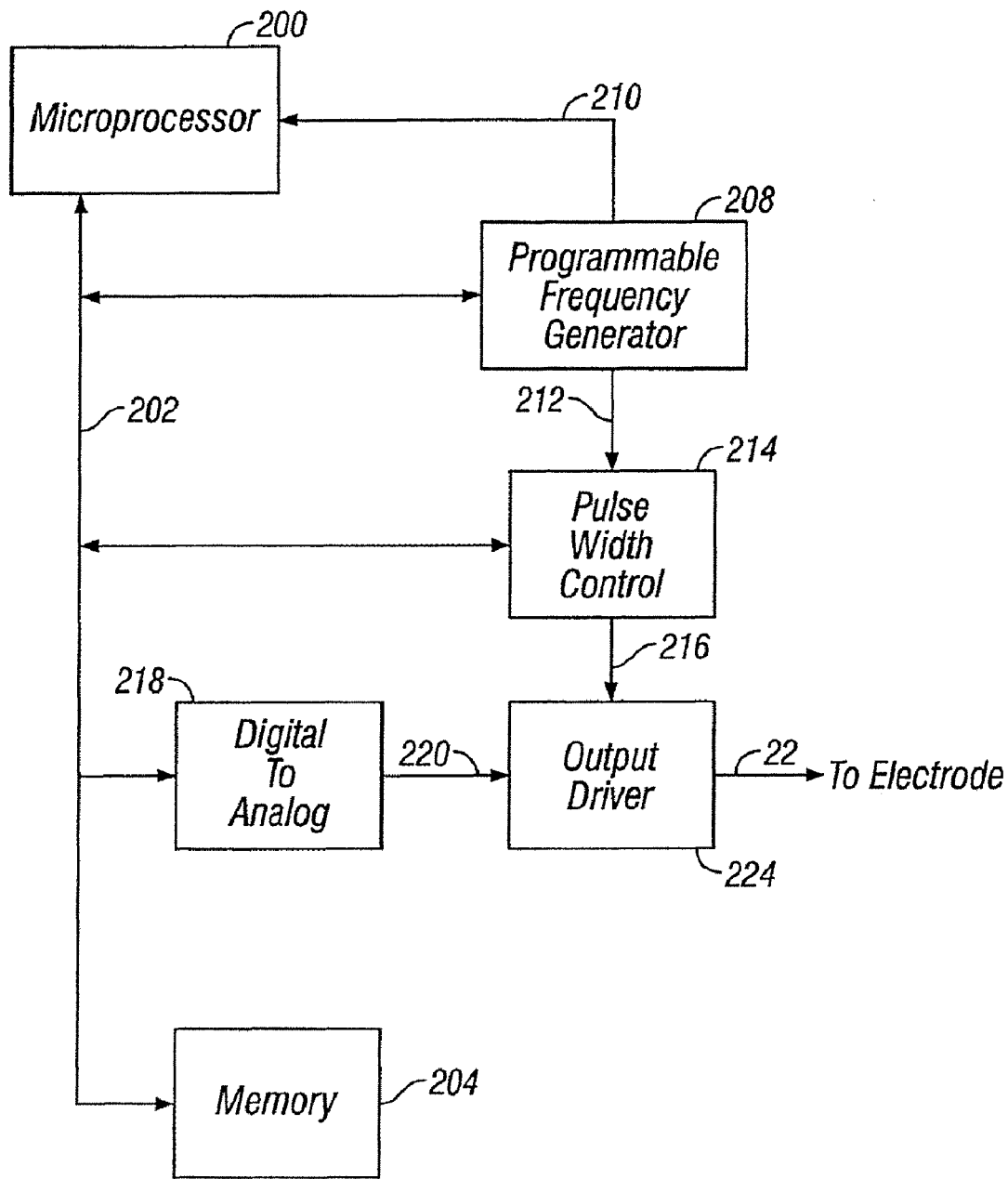
FIG. 5 is a schematic block diagram of a system in accordance with an illustrative embodiment of the invention.

FIG. 5 is a schematic block diagram of a portion of signal generator 10 in accordance with an illustrative embodiment of the present invention. Microprocessor 200 controls the amount of stimulation that will be supplied to the patient based on the input criteria from the clinician. The amounts of stimulation are applied through an output driver 224.

The stimulus pulse frequency is controlled by programming a value to a programmable frequency generator 208 using bus 202. The programmable frequency generator provides an interrupt signal to microprocessor 200 through an interrupt line 210 when each stimulus pulse is to be generated.

The amplitude for each stimulation pulse is programmed to a digital to analog converter 218 using bus 202. The analog output is conveyed through a conductor 220 to an output driver circuit 224 to control the neural-stimulation amplitude.

Microprocessor 200 also programs a pulse width control module 214 using bus 202. The pulse width control module provides an enabling pulse of duration equal to the desired stimulation-pulse width via a conductor 216. Pulses with the selected characteristics are then delivered from device 10 through cable 22 and lead 22A to the specified region of the brain.

As described in more detail below, in addition to stimulation parameters discussed above, an electrode firing pattern and/or electrode-firing-polarity conditions can also be programmed into and controlled by the microprocessor 200.

Figure 6:
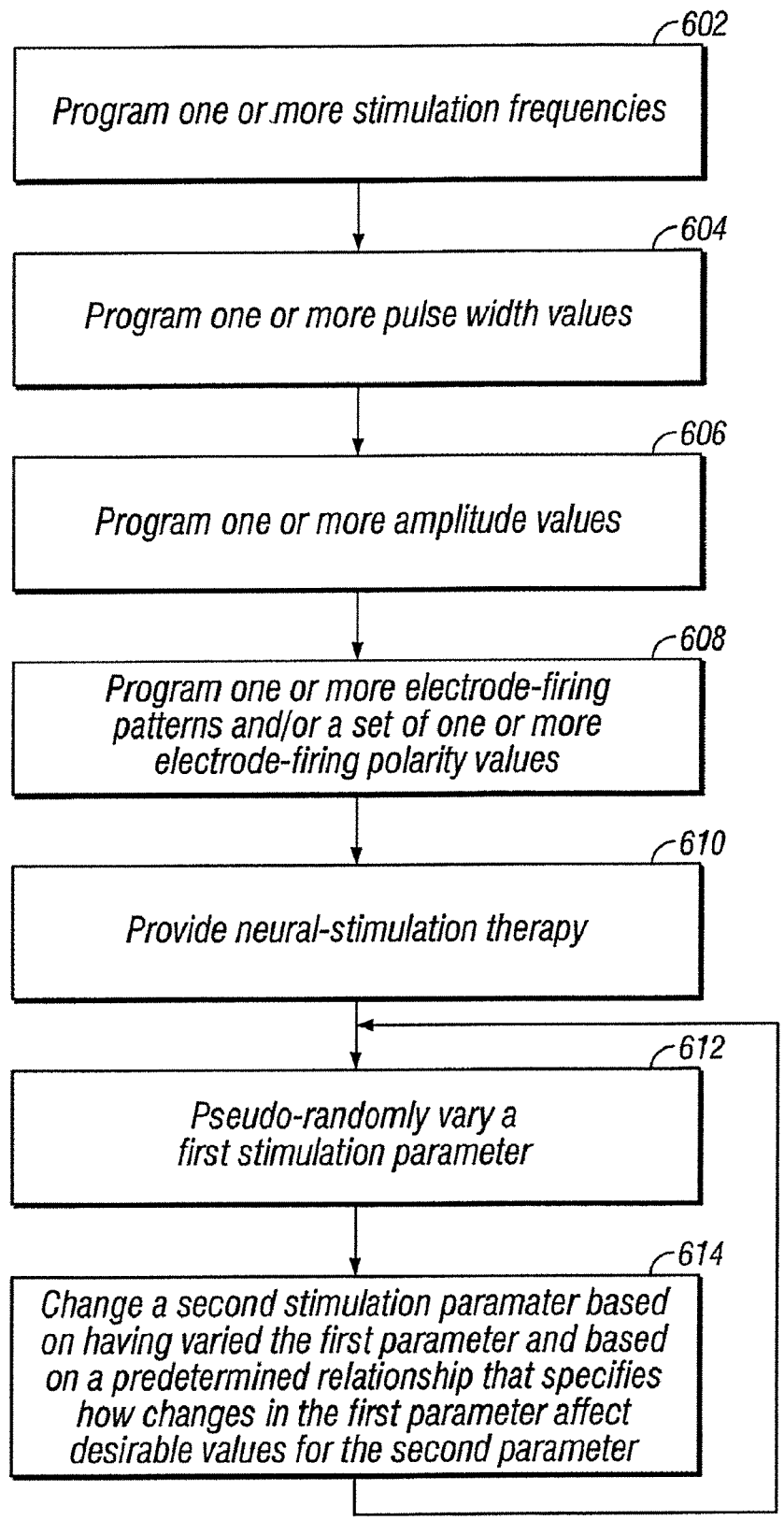
FIG. 6 is a flow chart of an algorithm for generating stimulation pulses with varying stimulus parameters.

Microprocessor 200 executes an algorithm shown in FIG. 6 to provide neural stimulation in accordance with an illustrative embodiment of the invention. Those of ordinary skill in the art will recognize that FIG. 6 represents an iterative process, which may be executed many times per second or may be executed, for example, once every several minutes.

A clinician may program certain parameters into the memory 204 of the implanted stimulation device 10. The clinician programs ranges of values for the following parameters of a patient's treatment plan in the following corresponding steps: one or more frequency values in step 602, one or more pulse-width values in step 604, one or more amplitude values in step 606, and one or more electrode firing patterns and/or a set of one or more electrode-firing polarity conditions in step 608. As an optional safety feature, values that exceed the capabilities of stimulator 10 are not stored in memory 204. For example, the clinician could program a range of 100-150 Hz for the stimulus frequency for the treatment of tremor with thalamic stimulation, while for the treatment of pain with thalamic stimulation the frequency range might be programmed from 50-80 Hz.

Figure 7:
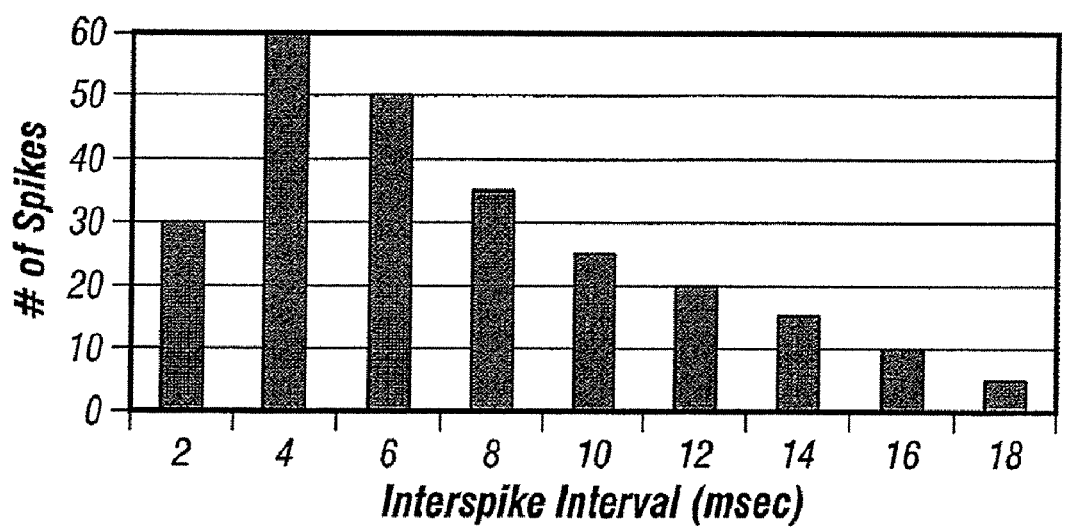
FIG. 7 is a histogram illustrating a skew-left-distribution interspike interval.

In step 610, the algorithm starts providing neural-stimulation therapy. In step 612, a first stimulation parameter, such as frequency, is pseudo-randomly varied. The decision to pseudo-randomly vary the first stimulation parameter could depend on the range and shape of the ISI distribution as programmed by the clinician. The ISI distribution can be selected from a group of choices, such as a normal distribution, a skew-left distribution, a skew-right distribution, and a bi-modal or bursting distribution. FIG. 3 depicts an example of a normal ISI distribution. FIGS. 7 and 8 are histograms that depict example skew-left and skew-right ISI distributions, respectively, that could be programmed by a patient's treating physician or any other clinician. FIG. 9 is a histogram that depicts an example bi-modal ISI distribution. In each type of ISI distribution depicted in FIGS. 3 and 7-9, the average firing frequency for a given period of time is the same. The temporal firing pattern however is different, with short, medium, or long ISI's predominating. In the bimodal distribution, the neuron would be exhibiting a common firing pattern known as "bursting" with short high frequency bursts of spikes interspersed over periods of relative inactivity. These different types of stimulation patterns advantageously produce significant variation in the temporal and spatial activation within the neuronal population. By varying the temporal and spatial activation in this manner, significantly different clinical effects can be produced.

At step 612, at least a first of the stimulation parameters is pseudo-randomly varied. At step 614, the value of a second stimulation parameter is changed based upon having pseudo-randomly varied the first stimulation parameter and based upon a predetermined relationship that specifies how changes in the first parameter affect desirable values for the second parameter. The predetermined relationship may be substantially similar to a strength-duration curve for neural excitation, such as the strength-duration curve of FIG. 4. If the ISI pattern were varied from a normal to a bimodal pattern, the stimulation amplitude may have to be varied, in a predetermined manner, to account for the change in temporal activation patterns which may have more or less clinical effect, as previously described.

For example, a clinician could program the stimulator to provide stimulation having an average frequency of 100 Hz over a specific period of time, such as a specific two-minute interval. The clinician could also program the stimulator to produce an ISI distribution corresponding to treatment frequencies ranging from 70 Hz to 130 Hz and select a specific distribution pattern (e.g., normal, skewed, bimodal). So during a two minute interval, while the stimulation frequency will average 100 Hz, it will also vary over a specified range. The physician could then choose to program a second ISI distribution for a subsequent time period, and so on, so that the stimulus pattern changes over time. Coincident with the changes in the ISI distribution, the stimulus amplitude may be varied, in a predetermined manner that corresponds with predetermined changes in clinical efficacy, as described above. Those of ordinary skill in the art will recognize that the invention contemplates multiple alternative choices for ISI distributions and should not be limited to the example distributions listed.

Similarly, variations around a mean value for amplitude, and pulse width may also be programmable and may be based upon ranges determined by the clinician during adjustment of the device. In this manner, the development of physiologic tolerance may be avoided, and it may also be possible to select temporal and spatial stimulation patterns that avoid excess use of implanted battery current and/or avoid undesired side effects of stimulation that may occur, while maintaining the desired therapy efficacy.

The neural-stimulator electrode-firing conditions may be varied to prevent patient adaptation to treatment. The electrode-firing-condition changes could be implemented by changing electrode states between off, cathode, or anode, in a predetermined manner. The altered polarities would result in changes to the delivered electrical field and thus the spatial patterns of neurons that are affected. For instance, referring to FIG. 9A, in a first step, electrodes 900 and 902 of lead 904 are programmed as anodes, and electrode 906 is programmed as a cathode. Stimulation having a predetermined stimulus amplitude and pulse width is delivered. The stimulated neural tissue is shown as a sphere surrounding the cathode. In a following step, the polarities of the electrodes are reversed, and the spatial pattern of the stimulated tissue changes, as shown in FIG. 9B. Co-incident with this change in the spatial pattern, the stimulation amplitude would be varied, in a pre-determined manner, to achieve the desired clinical efficacy. A virtually infinite number of electrode combinations and stimulus-parameter settings (including amplitude, pulse width, and frequency) could be determined that provide a desired clinical efficacy. A clinician can then select any number of these electrode combinations and stimulus-parameter settings. These combinations of parameters could then be varied in a pseudo-random manner to create different spatial regions of excitation, thereby preventing development of tolerance due to the continuous stimulation of the same population of neurons and, in turn, improving the efficacy of DBS and other therapies involving electrical stimulation of the nervous system.

While the invention has been described with respect to specific examples including presently preferred modes of carrying out the invention, those skilled in the art will appreciate that there are numerous variations and permutations of the above described systems and techniques that fall within the spirit and scope of the invention as set forth in the appended claims and their equivalents.

I claim:

1. A neural-stimulation system for varying stimulation parameters, comprising:
   at least one neural-stimulation lead, wherein at least one of the leads has at least one neural-stimulation electrode; and
   a neural-stimulation device operatively coupled to the at least one neural-stimulation lead, wherein said device includes a strength-duration curve of neural excitation, wherein the strength-duration curve of neural excitation contains measured stimulation-amplitude values at corresponding stimulation-pulse durations that achieve reduction of tremor via thalamic stimulation, wherein the neural-stimulation device is configured to:
   provide neural stimulation having a plurality of stimulation parameters including a stimulation amplitude, a stimulation frequency, a stimulation pulse duration, an electrode-firing pattern, and a set of one or more electrode-polarity-firing conditions,
   pseudo-randomly vary at least a first of the stimulation parameters, and
   change a value of a second of the stimulation parameters based upon having varied the first stimulation parameter and based upon the strength-duration curve of neural excitation.

2. The neural-stimulation system of claim 1 in which the neural stimulation device pseudo-randomly varies at least the first of the stimulation parameters within a predetermined range.

3. The neural-stimulation system of claim 1 in which the neural stimulation device pseudo-randomly varies at least the first of the stimulation parameter to produce a plurality of neuron-firing patterns selected from the group consisting of: a substantially-normal-distribution neural-firing pattern, a skew-left-distribution neural-firing pattern, a skew-right-distribution neural-firing pattern, and a bimodal-bursting-distribution neural-firing pattern.

4. The neural-stimulation system of claim 1 in which the neural stimulation device pseudo-randomly varies at least the first of the stimulation parameter sufficiently to avoid development of physiological tolerance to the neural-stimulation.

5. A neural-stimulation system for varying stimulation parameters, comprising:
   at least one neural-stimulation lead, wherein at least one of the leads has at least one neural-stimulation electrode; and
   a neural-stimulation device operatively coupled to the at least one neural-Stimulation lead, wherein said device includes a strength-duration curve of neural excitation, wherein the strength-duration curve of neural excitation contains measured stimulation-amplitude values at corresponding stimulation-pulse durations that achieve reduction of tremor via thalamic stimulation, wherein the neural-stimulation device is configured to:
   provide neural stimulation having a plurality of stimulation parameters;
   pseudo-randomly vary at least a first of the plurality of stimulation parameters; and
   change a value of a second of the plurality of stimulation parameters based upon having varied the first stimulation parameter and based upon the strength-duration curve of neural excitation.

6. The neural-stimulation system of claim 5, wherein the neural-stimulation device pseudo-randomly varies the first stimulation parameter within a predetermined range.

7. The neural-stimulation system of claim 5, wherein the neural-stimulation device includes an implantable pulse generator.

8. The neural-stimulation system of claim 5, wherein the neural stimulation device pseudo-randomly varies at least the first of the stimulation parameter to produce a plurality of neuron-firing patterns selected from the group consisting of: a substantially-normal-distribution neural-firing pattern, a skew-left-distribution neural-firing pattern, a skew-right-distribution neural-firing pattern, and a bimodal-bursting-distribution neural-firing pattern.

9. The neural-stimulation system of claim 5, wherein the neural stimulation device pseudo-randomly varies at least the first of the stimulation parameter sufficiently to avoid development of physiological tolerance to the neural-stimulation.

10. The neural-stimulation system of claim 5 in which:
    the pseudo-randomly varying of the at least a first of the stimulation parameters is adapted to vary at least a first stimulation parameter selected from the group consisting of stimulation amplitude, a stimulation pulse duration, an electrode-firing pattern, and a set of one or more electrode-polarity-firing conditions; and
    the changing a value of a second stimulation parameter is based at least in part upon having pseudo-randomly varied the first stimulation parameter and based upon the measured strength-duration curve that specifies how changes in the first parameter affect desirable values for the second parameter, the second parameter selected from the group consisting of stimulation amplitude, a stimulation frequency, a stimulation pulse duration, an electrode-firing pattern, and a set of one or more electrode-polarity-firing conditions.

11. The neural-stimulation system of claim 5 in which:
    the pseudo-randomly varying of the at least a first of the stimulation parameters is adapted to vary at least a first stimulation parameter selected from the group consisting of stimulation amplitude and stimulation pulse duration; and the changing a value of a second stimulation parameter is based upon at least in part having pseudo-randomly varied the first stimulation parameter and based upon the measured strength-duration curve that specifies how changes in the first parameter affect desirable values for the second parameter, the second parameter selected from the group consisting of stimulation amplitude, a stimulation frequency, a stimulation pulse duration, an electrode-firing pattern, and a set of one or more electrode-polarity-firing conditions.

\* \* \* \* \*